United States Patent [19]

Matsuo

[11] Patent Number: 4,743,966

[45] Date of Patent: May 10, 1988

[54] ENDOSCOPE APPARATUS FOR IMAGING INTERNAL PORTIONS OF A PATIENT'S BODY

[75] Inventor: Satoshi Matsuo, Ootawara, Japan

[73] Assignee: Kabushiki Kaisha Toshiba, Kawasaki, Japan

[21] Appl. No.: 1,566

[22] Filed: Jan. 8, 1987

[30] Foreign Application Priority Data

Jan. 10, 1986 [JP] Japan .................................. 61-3152

[51] Int. Cl.$^4$ .............................................. H04N 7/18
[52] U.S. Cl. ..................................... 358/98; 358/211; 128/6; 128/712
[58] Field of Search ................. 358/98, 211, 228, 166; 128/6, 696, 697, 700, 710, 712

[56] References Cited

U.S. PATENT DOCUMENTS 4,572,202  2/1986  Thomenius ..................... 358/112 X
4,597,381  7/1986  Oumi et al. ....................... 358/98 X
4,654,701  3/1987  Yabe ..................................... 358/98

Primary Examiner—Howard W. Britton
Assistant Examiner—Victor R. Kostak
Attorney, Agent, or Firm—Schwartz, Jeffery, Schwaab, Mack, Blumenthal & Evans

[57] ABSTRACT

An endoscope device according to the present invention includes an endoscope used to pick up images at an object portion in a body cavity that is pulsating at irregular rates and is illuminated by a light source, a memory device for storing the date of picked-up images sequentially, and a display device for displaying the images based on the data of picked-up images. The endoscope device further includes an electrocardio signal processor for generating a delay signal corresponding to the latest phase of pulsation in the object portion in accordance with an electrocardio signal, and a system controller for controlling the light source, the memory device, and the display device such that the light is periodically emitted from the light source, the writing operation of the memory device is interrupted and the image retained in the memory is displayed on the display device as a freeze appearance in accordance with the delay signal.

10 Claims, 5 Drawing Sheets

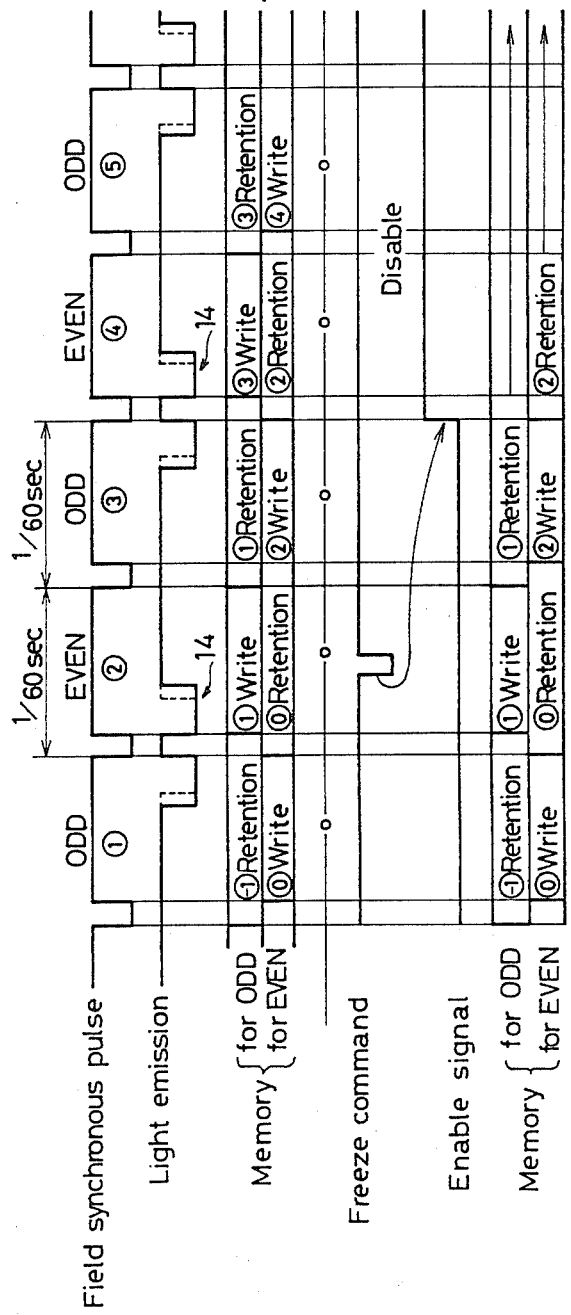

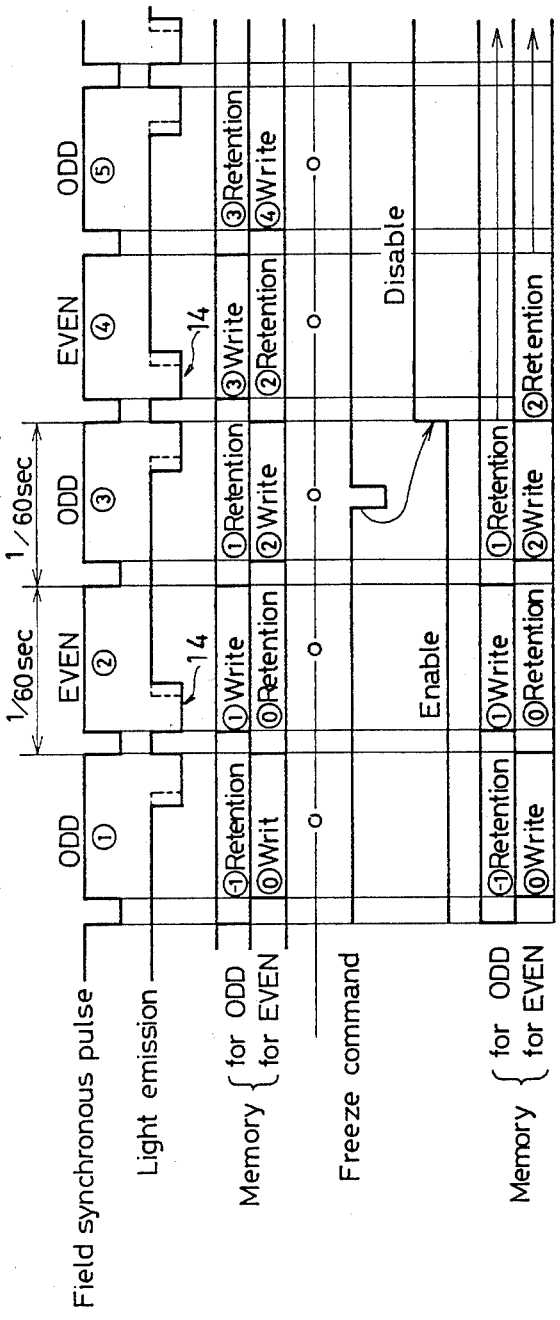

ENDOSCOPE APPARATUS FOR IMAGING INTERNAL PORTIONS OF A PATIENT'S BODY

BACKGROUND OF THE INVENTION

1. Field of the Invention

The present invention relates to an endoscope apparatus using an image pickup device which is inserted in a body cavity.

2. Description of the Prior Art

A typical conventional endoscope apparatus used a camera attached to the eyepiece of a fiberscope having an image guide comprising optical fibers, thereby picking up the images of a body cavity. At that time, ambiguous images were often created due to movement of the body cavity, etc., which used to be solved by increasing the shuttering rate of the camera. However, a TV monitor is normally used as a display means with an endoscope system using the solid-state image pickup device. Therefore, a minimum shuttering rate of the camera is 1/30 sec to 1/60 sec (these values correspond to the period of the TV monitor per frame or field).

In addition, said time period of 1/30 sec to 1/60 sec should be synchronized with the frame frequency of the TV monitor or field frequency.

Such shuttering operation cannot be practically realized because a shutter is mechanically driven.

Consequently, the foregoing image pickup requires such a series of operations that first the TV monitor is set to blanking state then the shutter is opened to display only the image of a required frame or field, then again set to blanking state while the shutter is then returned to close.

Such operations not only are complicated but also require that the iris be opened wide according to the luminance of the TV monitor and film sensitivity. Therefore, focal depth becomes shallower, making it very difficult to reduce out-focusing for the image displayed on the TV monitor.

Another method is also proposed and used to pick up images, in which the image information for a frame or field is stored in the memory, sent to and displayed on the TV monitor while displayed image is being picked up.

At this time, a problem is how long time is required to collect image information to be stored in the memory. Referring to FIG. 1 (a) in which light is emitted for each field, for example, time for collecting image information per frame becomes $(1/60+T)$ sec where $t_{VD}$ is the pulse width of its synchronous pulse VD and T is the light emitting time interval of a light source for picking up images.

Referring to FIG. 1 (b) where light is emitted at the end of a field and the beginning of the next field for collecting images, on the other hand, time for collecting image information per frame becomes $(t_{VD}+2T)$ sec.

In either case, time for emitting light is T sec per field. However, time required for structuring image for a frame with the case of FIG. 1 (b) is much shorter.

Consequently, the case of FIG. 1 (b) brings out the image with less out-focusing.

Another problem is long or short time for emitting light as described above. With this emitting time T shorter, the foregoing time required for forming a frame can be reduced further. However, with this time reduced in excess, ratio S/N deteriorates because of the performance characteristics of the solid-state image pickup element.

SUMMARY OF THE INVENTION

The objective of the present invention is to provide an endoscope apparatus that can create the images of excellent qualities without accompanying S/N ratio deterioration. An endoscope device according to the present invention relates to an endoscope device in which an endoscope having a light source for periodically illuminating an object portion of a body cavity and a solid-state image pickup device is used to pickup images at a predetermined portion in a body cavity that is pulsating at irregular rates and stores the data of piokedup images sequentially in a memory device and, based on said data of picked-up images, displays images on a display device. The device of the present invention comprises a electrocardio signal processor for generating a delay signal corresponding to the latest phase of pulsation in the object portion in accordance with a pulsation detecting signal, and a system controller constructed to control so as to emit periodically the light from the light source interrupt the writing operation of the memory, and display the retained image in the memory as a freeze appearance in accordance with the delay signal.

These and other objects, features and advantages of the present invention will be more apparent from the following description of a preferred embodiment, taken in conjunction with the accompanying drawings.

BRIEF DESCRIPTION OF THE DRAWINGS

FIG. 1 (b) is another timing chart for showing the relationship between the field synchronous pulse and light emission with the solid-state image pickup device;

FIG. 4 (a) is a timing chart showing the relationships between field synchronous pulse in the apparatus, light emission, freeze command and enable signal of the solid-state image pickup device and writing and retention in the memory device;

FIG. 4 (b) is a timing chart that shows a case where said freeze command is issued at another timing; and FIG. 5 is a waveform showing another aspect of the enable signal.

DESCRIPTION OF THE PREFERRED EMBODIMENTS

Figure 1A:
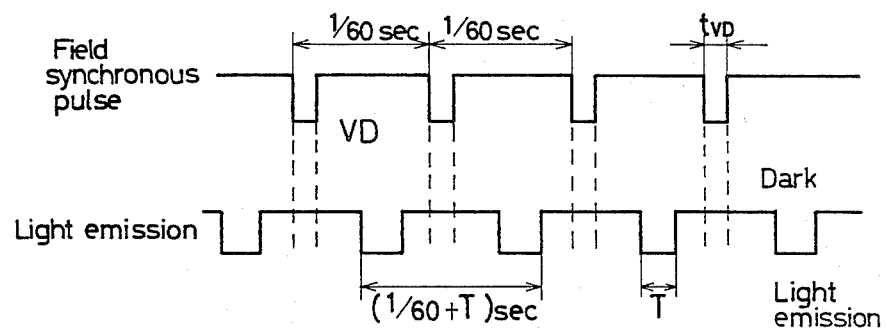
FIG. 1 (a) denotes a timing chart showing the relationship between the field synchronous pulse and light emission with the solid-state image pickup device.
Figure 1B:
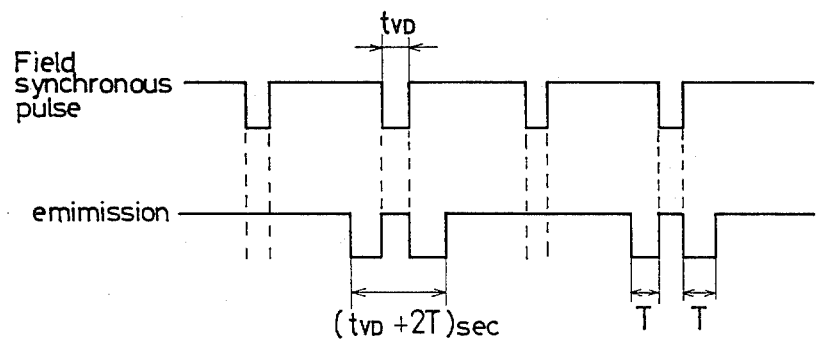
Figure 2:
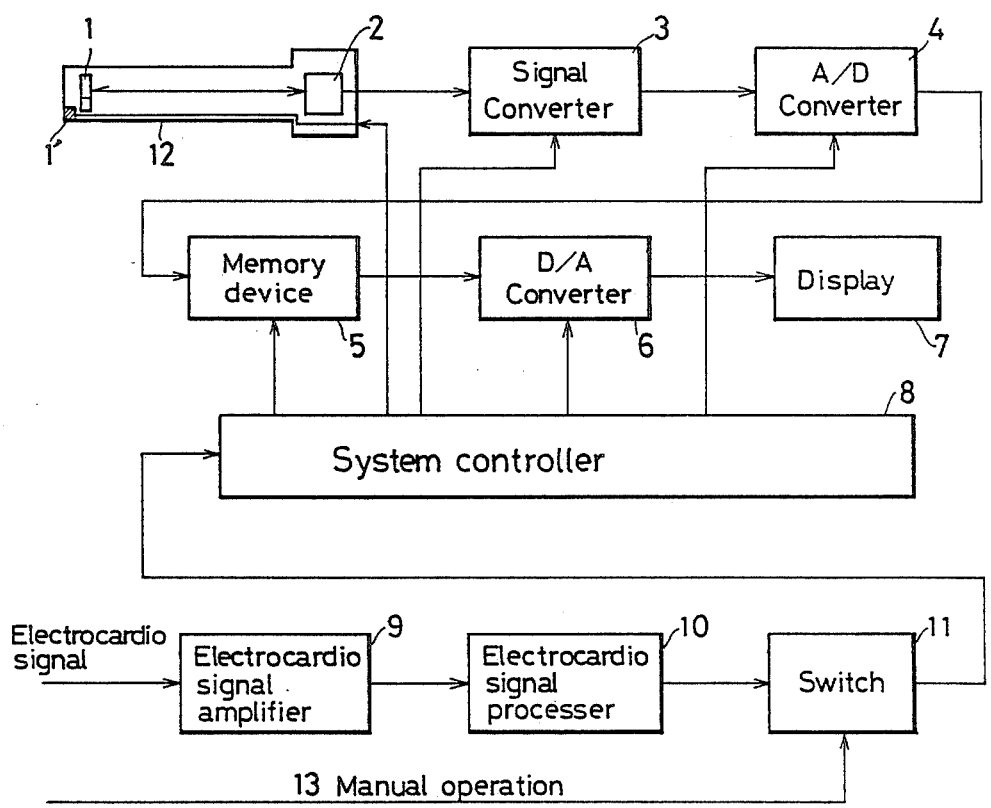
FIG. 2 is a block diagram showing an embodiment of the present invention.

An embodiment shown in FIG. 2 comprises a solid-state image pickup device 1 adapted to pickup an image of the body cavity at the top portion, an endoscope 12 provided with an image device controller 2 that supplies power to said solid-state image pickup device 1 and acquires signals from said device 1 and a light source 1' for illuminating an object portion of the body cavity with a predetermined frequency described follow, a signal converter 3 that signals acquired by said image pickup controller 2 to TV signals (composite signals or RGB signals), a A/D converter 4 that converts the output from said signal converter 3, a memory device 5 that stores and retains the output from said A/D converter 4, a D/A converter 6 that converts the signals read from a memory device 5 again to analog signals, a display device 7 for collecting and displaying the output from a D/A converter 6 such as TV monitor, a system controller 8 that controls said signal converter 3, A/D converter 4, memory device 5 and D/A converter 6, an electrocardio signal amplifier 9 that collects the electrocardio signals from an examining object. The endoscope apparatus further comprises an electrocardio signal processor 10 that detects the referential signal of said examining object based on the amplified electrocardio signals sent from said electrocardio signal amplifier 9 and generates delay signal (delay pulse) having a predetermined time delay from detected referential signal and a switch 1 that switches said delay pulse sent from said electrocardio signal processor 10 and the external freeze instruction signal (manually operated pulse according to the intention of the operator) 13 and sends either said pulse or said command to said system controller 8. And, the generating timing of the delay signal corresponds to a latest phase of pulsation in the object portion of the body cavity.

Said memory device 5 comprises 2 memory units for the ODD and EVEN fields, while having a memory capacity for a frame (for 2 fields). For this purpose, a memory device corresponding to 2 frames may be prepared and used alternatively on each frame.

In addition, a system controller 8 controls said memory units for the ODD and EVEN fields of said memory device 5 such that the data is rewritten and retained alternatively, by sending rewriting control signals and retention control signals. Furthermore a system controller 8 sends enable signals that determine whether rewriting or retaining status is to be continued or stopped to establish frozen status, in accordance with a freeze instruction signal.

Figure 3:
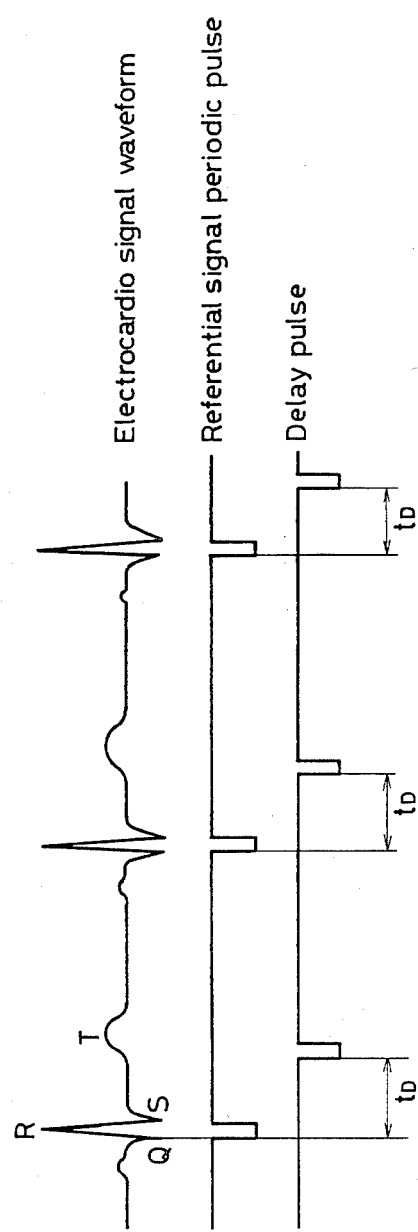
FIG. 3 shows the electrocardio waveform, referential synchronous pulse and delay pulse waveform associated with the apparatus according to the present invention.

The operations and functions of the apparatus structured in the above are described referring to the electrocardio waveform and the waveforms of the referential signal synchronous pulse and delay pulse shown in FIG. 3 and a timing chart shown in FIGS. 4 (a), (b) including field synchronous pulse, emission of light source 1' for the image pickup device, rewriting and retention of data in said memory device 5, generation of a freeze command 13 and the enable signal.

The image pickup device controller 2 drives the light source 1' to emit light for a solid image pickup device 1 inserted in the examining object at the end of period (1) for the ODD field and the beginning of period (2) for the EVEN field, therefore the solid image pickup device pickup so shoot the image of a predetermined position of the examining object.

An image shot in period (1) for the ODD field (nominated as the first image) is converted to electrical signal by solid-state image pickup device 1 then sent to signal converter 3 via image pickup device controller 2, in which said first signal is converted to TV signal. Said TV signal is further converted to digital signal in A/D converter 4, then sent to memory device 5 controlled by system controller 8, where said digital signal is written as the first image data at a timing synchronous to period (2) for said EVEN field. Said first image data is retained in memory device 5 during period (3) for the next ODD field.

Another image shot in period (2) for the EVEN field (nominated as the second image) is, on the other hand, sent to memory device 5 in a process similar to the above, in which said image is written in said memory device 5 as the second image data at a timing synchronous to period (3) for the EVEN field. Said second image data is retained in memory device 5 during the next period (4) for the EVEN field.

As described above, images are picked up using endoscope 12 while writing and retaining image data based on each shot image sequentially at predetermined timing. Image data per frame, comprising image data in the ODD and EVEN fields as written and retained in memory device 5, is sent to D/A converter 6 under the control of the system controller 8, in which said image data is converted to analog signals, then sent to a display device 7 and displayed thereon.

Consequently, images displayed in display device 7 sequentially change in the aspect of display frame by frame.

On the other hand, said electrocardio signal amplifier 9 acquires cardio signals from an examining object, amplifies and sends to an electrocardio signal processor 10. Said electrocardio signal processor 10 acquires cardio waveform signal including the referential signal shown in FIG. 3 based on amplified electrocardio signal. In addition, said processor 10 generates the referential signal synchronous pulse based on the referential signal of said cardio waveform signal and the delay pulse with a predetermined time delay of $t_D$ from said referential signal synchronous pulse.

Said delay pulse is sent to said system controller 8 via switch 11. System controller 8 issues freeze command at a predetermined timing based on the delay pulse and the freeze instruction signal and a instruction signal to the light source 1' simultaneously with the delay pulse described before. In addition, said controller 8 activates the enable signal to "HIGH" when writing of the second image data into said memory for the even field is completed, while terminating to write data into image memory device 5. Thereby, the memory for the ODD field continues to retain the first image data, while the memory for the EVEN field continuing the status of retaining the second image data. In other words, image data for a frame, comprising the first and second image data, is stored in image memory device 5. Said image data is converted to analog signal by D/A converter 6 and sent to display device 7 where said data is displayed as an image in freeze status.

FIGS. 4 (a) and (b) show timing charts when the freeze command is created in the ODD and EVEN fields, respectively.

Freeze image, that obtained, is picked up at the timing of latest pulsation among 1 heart pulse synchronously with the delay pulse, therefore high-quality image can be obtained without blurr.

Referring to FIG. 4 (a) where a freeze command based on the delay pulse, generated at a timing corresponding to the end of contraction period shown in FIG. 2, occurs in the EVEN field, a maximum time difference of (1/60+T) sec appears between freeze image and said delay pulse. In the case of FIG. 4 (b) where said command occurs in the ODD field, said time difference becomes, at maximum, (1/30+T) sec (as a frame image). Thereby, frozen image relates to a timing of rather less pulsation in the vicinity of contraction end period.

With a delay time $t_D$ shown in FIG. 3 set to 0, a freeze image in the vicinity of the end period of diastole.

At a timing of rather less pulsation, it is possible to be longer the light emitting time of the light source 1' as shown by a numeral 14 in FIG. 4 (a). Therefore, the ratio S/N of the solid image pickup device is improved.

Furthermore, the operator can manually freeze images by sending the manual operation pulse, corresponding to said delay pulse, while changing switch 11 referring to the image shown on display device 7, to system controller 8.

Moreover, said enable signal may be composed of pulse-like waveform that can be synchronous to data writing timing into memory device 5 shown in FIG. 5.

The present invention is not limited to the embodiment described above but can be modified in various ways within the scope of the claim. For example, referring to the device of FIG. 2, it is possible to omit signal passage due to manual operation and switch 11 while entering delay pulse from electrocardio signal processor 10 directly into system controller 8.

Another possible configuration for practical application is that electrocardio signal amplifier 9, electro signal processor 10 and switch 11 are not directly mounted in the apparatus but configured as another apparatus having the same functions, while applying the output signal from the other apparatus into system controller 8.

Still another possible method is that, with switch 11, a logical sum is taken for the output from electrocardio signal processor 10 and manual operation pulse and entered in system controller 8.

According to the present invention described above, the image at timing of slow pulsation can be set to frozen state for the purpose of photographing and displaying the image at an object portion of pulsating body under examination. Therefore, it is not required to greatly reduce the interval of light emission for the light source. Consequently, the present invention can provide an endoscope apparatus that creates high-quality recorded image without deterioration of S/N ratio or blurr.

Various modifications will become possible for those skilled in the art after receiving the teachings of the present disclosure without departing from the scope thereof.

What is claimed is:

1. An endoscope apparatus in which image data is obtained at an object portion in a body cavity that is pulsating at irregular rates and the image data is stored sequentially, comprising:
    image pickup means for obtaining image data of the object portion in the body cavity;
    storage means for storing sequentially the image data obtained by said image pickup means;
    display means for displaying the image data stored in said storage means;
    illuminating means for illuminating the object portion in the body cavity for said image pickup means;
    means for generating a delay signal corresponding to the latest phase of pulsation in the object portion in accordance with a pulsation detecting signal; and
    control means for controlling said illuminating means, storage means, and display means such that light is periodically emitted from said illuminating means, a writing operation of said storage means is interrupted, and the image data retained in said storage means is displayed as a frozen image on said data displayed means in accordance with the delay signal.

2. The endoscope apparatus as claimed in claim 1, wherein said control means controls said illuminating means and said image pickup means so as obtain image data of the object portion by illuminating said illuminating means synchronously with the delay signal.

3. The endoscope apparatus as claimed in claim 1, wherein the pulsation detecting signal of the body cavity is an electrocardio signal.

4. The endoscope apparatus as claimed in claim 1, wherein said control means controls said storage means such that the writing operation of said storage means is interrupted at a predetermined timing in accordance with the delay signal and a freeze instruction signal.

5. A freeze control device for use with an endoscope apparatus having; image pickup means adapted to pick up an image of an object portion in a body cavity that is pulsating at irregular rates, storage means for storing sequentially data of the image picked up by the image pickup means, display means for displaying the image data stored in the storage means, and illuminating means for illuminating the object portion for the image pickup means with light, said freeze control device comprising:
    means for generating reference pulse signals synchronized with a latest phase of pulsation in the object portion in accordance with a pulsation detecting signal;
    means for generating delay pulse signals delayed with a predetermined time from the reference pulse signals generated by said reference pulse signal generating means; and
    means for retaining data of an image synchronized with one of the delay pulse signals in the storage means as a frozen image.

6. The freeze control device for the endoscope apparatus as claimed in claim 5, wherein light is periodically emitted from the illuminating means in accordance with the delay pulse signals.

7. The freeze control device for the endoscope apparatus as claimed in claim 5, wherein the pulsation detecting signal is a electrocardio signal.

8. The freeze control device for the endoscope apparatus as claimed in claim 5, wherein said image retaining means comprises a system controller for sending retention control signals and rewriting control signals to the storage means such that the image data are retained and rewritten alternatively, and wherein the system controller is constructed for further sending an enable signal to the storage means to stop the rewriting of the data in accordance with the delay pulse signals and a freeze instruction signal from an operator such that the image synchronized with the delay pulse signal is retained in the storage means.

9. The freeze control device for the endoscope apparatus as claimed in claim 8, wherein the storage means comprises two memory units for ODD and EVEN fields.

10. A method of obtaining images in a body cavity that is pulsating at irregular rates, said method comprising the steps of:
    obtaining an image of the object portion in the body cavity with an image pickup device;
    storing sequentially the image in a storage device;
    displaying the image stored in said storage device;
    illuminating the object portion in the body cavity for for said image pickup device with an illumination device;
    generating a delay signal corresponding to the latest phase of pulsation in the object portion in accordance with a received pulsation detecting signal; and
    controlling said illumination device, storage device, and display device such that the light is periodically emitted from said illuminating device, a writing operation of said storage device is interrupted, and the image retained in said storage is displayed as a frozen image on said display device in accordance with the delay signal.

* * * * *